United States Patent [19]

Hommeltoft et al.

[11] Patent Number: 5,220,095
[45] Date of Patent: Jun. 15, 1993

[54] ALKYLATION PROCESS

[75] Inventors: Sven I. Hommeltoft, Hillerod; Haldor F. A. Topsoe, Vedbaek, both of Denmark

[73] Assignee: Haldor Topsoe A/S, Denmark

[21] Appl. No.: 626,956

[22] Filed: Dec. 13, 1990

[30] Foreign Application Priority Data

Dec. 18, 1989 [DK] Denmark ................. 1-6439
Jun. 8, 1990 [DK] Denmark ................. 2-1402

[51] Int. Cl.⁵ ............................. C07C 2/56; C07C 2/58
[52] U.S. Cl. .................................. 585/720; 585/721; 585/730; 502/20
[58] Field of Search .................... 585/720, 721, 730; 502/20

[56] References Cited

U.S. PATENT DOCUMENTS

| 2,313,103 | 3/1943 | Thomas | 196/10 |
| 3,778,489 | 12/1973 | Parker | 585/730 |
| 3,976,759 | 8/1976 | Bennett et al. | 502/20 |
| 4,071,576 | 1/1978 | Behrmann et al. | 585/730 |
| 4,073,821 | 2/1978 | Siskin | 585/730 |
| 4,508,618 | 4/1985 | Olah | 208/134 |
| 4,783,567 | 11/1988 | Kocal | 585/464 |

OTHER PUBLICATIONS

*Grant & Hackh's Chemical Dictionary*, 5th ed., McGraw-Hill Book Co.: New York (1987), p. 561.

*Primary Examiner*—Anthony McFarlane
*Assistant Examiner*—Nhat D. Phan
*Attorney, Agent, or Firm*—Ostrolenk, Faber, Gerb & Soffen

[57] ABSTRACT

A process for liquid phase alkylation of a hydrocarbon substrate with an olefinic alkylating agent comprising the steps of passing a process stream of the hydrocarbon substrate and alkylating agent at alkylating conditions through a fixed bed alkylation reactor of particulate polar contact material in the presence of a fluorinated sulfonic acid catalyst.

11 Claims, 2 Drawing Sheets

ALKYLATION PROCESS

BACKGROUND OF THE INVENTION

1. Field of the Invention

The present invention relates to the alkylation of hydrocarbons, and in particular to liquid phase alkylation of aliphatic hydrocarbons in the presence of a supported liquid acid catalyst.

2. Description of the Prior Art

Acid catalyzed alkylation of aliphatic hydrocarbons with olefinic hydrocarbons is a well known process for the preparation of high octane gasoline products. In the past, alkylation of hydrocarbons has been accomplished in liquid phase by mixing paraffins and olefins in the presence of a strong acid catalyst and stirring the mixture until the alkylation reaction was completed. Such a batch process layout requires large reaction volumes and thorough mixing of the alkylation mixture by mechanical mixing means in order to provide intimate contact between the acid catalyst, the reacting hydrocarbons, and the olefinic alkylating agent.

Although being very efficient, a major drawback of the known acid catalysts are their environmental and health risk, when used in large amounts such as in the known batch processes.

An alkylation process using minor amounts of liquid hydrofluoric acid or sulfuric acid is disclosed in U.S. Pat. No. 4,783,567. By the disclosed process, a reaction mixture of an olefinic alkylating agent and a hydrocarbon substrate is contacted with liquid hydrofluoric acid or sulfuric acid in a fixed bed reaction zone comprising particulate contact material. In the reaction zone an emulsion is formed, which is sustained by agitation or turbulence for a length of time, after which it is passed to a settling zone, where separated liquid acid and hydrocarbon phases are formed and withdrawn. The resulting alkylation product has a high octane number, which increases with increasing reactor packing volume.

A disadvantage of the disclosed process, however, is the use of hydrofluoric acid or sulfuric acid alkylation catalysts. Besides being hazardous materials as mentioned hereinbefore, sulfuric acid and hydrofluoric acid are rather unstable or aggressive compound under the reaction conditions used in the alkylation process. At ambient conditions, hydrofluoric acid is a volatile gas, which necessitates the alkylation process to be carried out at low temperatures or at elevated pressure. While sulfuric acid is a liquid with a high boiling point and much easier to contain in the event of an accident, it is consumed in considerable amounts during the process by reduction to volatile sulfur dioxide and other unwanted products.

SUMMARY OF THE INVENTION

It has now been found that fluorinated sulfonic acids are efficient catalysts during the alkylation of hydrocarbons with olefins. Besides having less volatile compounds with appreciatively minor environmental and health risk than hydrofluoric acid, the fluorinated sulfonic acids, when used as alkylation catalysts, do not disintegrate during the alkylation reaction, as is the case for sulfuric acid.

Pursuant to this finding, it is an object of the present invention to provide process for liquid phase alkylation of a hydrocarbon with an olefinic alkylating agent in the presence of a fluorinated sulfonic acid.

In accordance with the present invention, an improved process for liquid phase alkylation of a hydrocarbon substrate with an olefinic alkylating agent is provided, comprising the step of passing a process stream of hydrocarbon substrate and the alkylating agent at alkylating conditions through a fixed bed alkylation reactor of particulate polar contact material in the presence of a fluorinated sulfonic acid catalyst.

As an advantageous feature of the invention it is possible to separate and reuse the fluorinated sulfonic acid catalyst from the alkylated process stream by continuous extraction with water. After separation the diluted acid catalyst is recovered in a following distillation and concentration step in the presence of concentrated sulfuric acid and distillation before recycling to the alkylation reactor.

Based on different migration speeds of a nonpolar hydrocarbon process stream and the very polar sulfonic acid catalyst on polar contact materials, a preferred embodiment of the invention comprises the further process steps of establishing within a confined area of the polar contact material, a movable reaction zone with the fluorinated sulfonic acid catalyst adsorbed on the contact material;

passing a process stream of the hydrocarbon substrate and the olefinic alkylating agent at alkylating conditions in one flow direction through the reaction zone and the residue of the polar contact material; and optionally, periodically reversing the flow direction of the process stream as the reaction zone has passed substantially the whole length of the contact material.

Preferred fluorinated sulfonic acid catalysts for use in the inventive process are trifluoromethanesulfonic acid and/or fluorosulfonic acid.

Compared to the known alkylation catalysts, the acidity of the fluorinated sulfonic acid catalyst is very high resulting in improved efficiency in the alkylation of hydrocarbons.

Due to the high efficiency and stability of the catalysts during the alkylation process small amounts of the acid applied on the contact material ensure high yields of alkylated products. Thus for instance, when using silica as a contact material, amounts of between 0.1 and 100 ml, preferably 1–50 ml and most preferred, 4–25 ml acid per volume contact material and per $cm_2$ cross-sectional area occupied by the contact material within the wall of a reaction vessel, will be sufficient to provide optimal alkylation rates.

Besides the above silica any of the polar and nonbasic refractory materials are suitable for use as contact materials in the inventive process. Preferred materials are silica, alumina, zirconia, titania, niobium oxides, tin oxides or mixtures thereof.

By interaction between polar groups of the contact material molecules and polar groups of the sulfonic acid molecule, the acid is adsorbed strongly on the contact material within a confined area, thereby providing the reaction zone for the alkylation reaction. The band width of adsorbed acid, wherein the alkylation reactions proceed is according to know chromatographic principles determined by the number of theoretical plates and the capacity factor of the contact material used.

Within the reaction zone, the process stream of hydrocarbon substrate comprising paraffins, such as $C^3$–$C^{10}$ isoalkanes, and olefinic alkylating agent typically comprising $C^2$–$C^{10}$ olefins, is converted at alkylating conditions to a product stream containing alkylated products by catalysis of the fluorinated sulfonic acid adsorbed on the contact material. The process stream may be passed through the alkylation reactor at temperatures of between −50° and 100° and at a pressure varying in the range of between 1–100 bar ibis. depending on the composition of the process stream and the actual reaction temperature.

The weight ratio of the hydrocarbon substrate to the alkylating agent in the process stream may, thereby, Vary between 1.5:1 and 30:1.

During the alkylation reaction, the acid catalyst, and, consequently, the reaction zone moves to a new position located nearer the outlet end of the alkylation reactor by interaction with the process stream flowing through and reacting in the zone.

As a theoretical explanation, the elution of the sulfonic acid is caused by reactions of the acid is caused by reactions of the acid catalyst with olefins in the process stream to a sulfonic acid ester, which is less polar than the original acid and more loosely adsorbed on the contact material in the reaction zone. The ester moves together with the process stream until it is cleaved to yield the free acid and a carboniumion, which reacts with the hydrocarbon substrate to form alkylated hydrocarbons.

The migration speed of the acid catalyst in the reactor and on the contact material is a mentioned hereinbefore much lower than the migration speed of the hydrocarbons in the process and product stream resulting in a very long elution time for the acid catalyst compared to the elution time for the hydrocarbons.

During the migration of the acid catalyst and the reaction zone on the contact material the catalytic activity of the fluorinated sulfonic acid is substantially retained and the acid is still catalytic active, when the reaction zone reaches the reactor outlet.

As further an advantageous feature of the inventive process it is possible based on the above principles, to reuse the acid as it reaches the outlet end of the alkylation reactor in a subsequent process cycle without recovery of the acid. Thereby the flow direction of the process stream introduced into the alkylation reactor is reversed and the reaction zone pushed towards the opposite end of the reactor by interaction with the process stream as described above.

Thus by periodically reversing the flow direction and pushing the reaction zone inside the reactor between the opposite ends of the contact material bed even very small amounts of acid catalyst ensure high yields of alkylated products without restitution or recovery of spent catalyst for a very long time on stream.

When reversing the flow direction of the process stream, a small volume of the stream introduced just before the flow reversal will not have passed through the reaction zone and consequently leave the reactor unconverted.

Thus in a further embodiment of the invention the volume of the process stream, which is withdrawn from the alkylation reactor during the reversion of the flow direction, is recycled to the inlet of the alkylation reactor.

Alternatively and instead of recycling a part of the process stream during the flow reversion, the stream leaving the alkylation reactor at the beginning of each process cycle may be conducted to a subsequent alkylation reactor and processed in similar manner as in the previous reactor.

In the following the invention will further be illustrated by reference to the drawings, in which Other features and advantages of the present invention will become apparent from the following description of the invention which refers to the accompanying drawings.

DETAILED DESCRIPTION OF THE INVENTION

Figure 1:
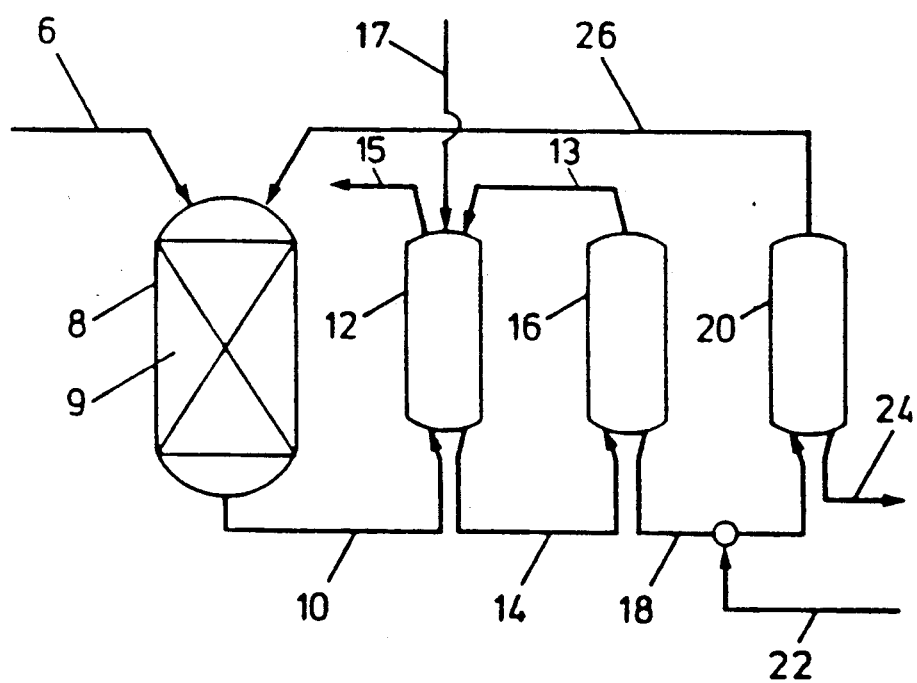
FIG. 1 represents a process diagram of one embodiment of the inventive process.

Referring not to FIG. 1, hydrocarbon feed comprising paraffins, such as $C^3$–$C^{10}$ isoalkanes, is passed on line 6 together with an $C^2$–$C^{10}$ olefin alkylating agent to an alkylation reactor 8. The reaction mixture passes through a fixed bed of particulate contact material 9 contained in the alkylation reactor 8.

The alkylation reaction may be carried out at a temperature of between −50° and up to 100° C., but temperatures lower than 40° C. are preferred. The pressure may thereby vary in the range of between 1–100 bar ibis., depending on the reaction temperature and the composition of the reaction mixture.

After a residence time of about 0.1–60 min. a product stream comprising the alkylated product containing small amounts of the acid catalyst is withdrawn from reactor 8 and conducted in line i0 to a scrubber unit 12. In unit 12 the stream of alkylated products is washed with water supplied on line 13 and 17 and flowing countercurrently to the product stream in unit 12.

During the washing step spent trifluoromethanesulfonic acid is recovered at the bottom of unit 12 and passed via line 14 to a distillation unit 16.

The washed product stream is withdrawn at the top of unit 12 in line 15.

In distillation unit 16 trifluoromethanesulfonic acid is concentrated by distillation at a temperature of about 215° C., which is the boiling point of the hydrated acid. Water distilling off in unit 16 is recycled to scrubber unit 12 through line 13. The concentrate from distillation tion unit 16 consisting mainly of trifluoromethanesulfonic acid hydrate is admixed in line 18 with concentrated sulfuric acid from line 22 in order to bring the hydrated acid to its dehydrated form.

The mixture of dehydrated acid and sulfuric acid is separated in distillation unit 20, wherein the anhydrous acid is distilled off at a temperature of about 167° C. The recovered and regenerated trifluoromethanesulfonic acid catalyst is then recycled in line 26 to the alkylation reactor 8. Used sulfuric acid is withdrawn from unit 20 on line 24.

The above represented flow scheme is simplified and various installations such as heat exchangers, pumps and valves, which are conventional parts of a process plant, are not taken into consideration. Various changes and additional process steps, such as recovery and working up of used sulfuric acid by distillation in a further process unit and recycling concentrated sulfuric acid to the trifluoromethanesulfonic acid hydrate leaving unit 16, may be performed without deviating from the scope of the present invention.

Figure 2:
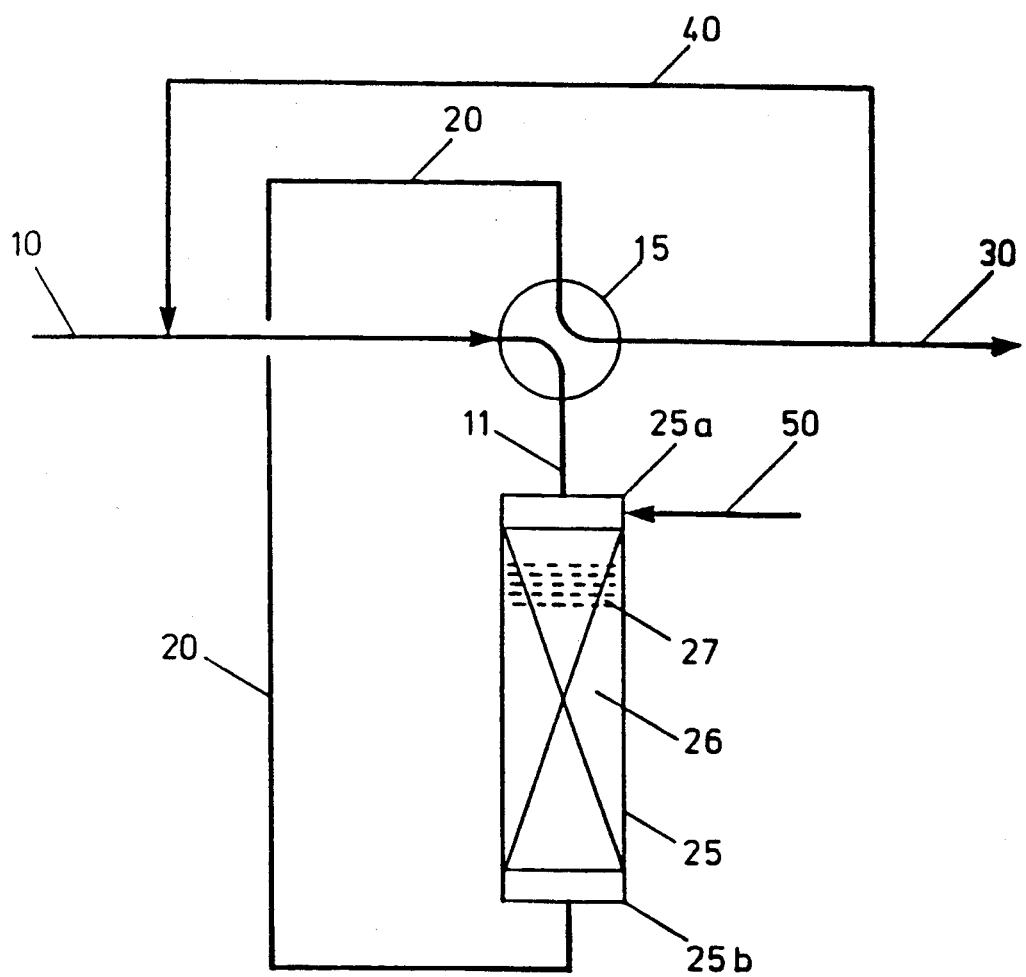
FIG. 2 is a schematic representation of a preferred embodiment of the alkylation process according to the invention.

FIG. 2 is a process diagram of an alkylation process, wherein the fluorinated alkylation catalyst is arranged as a moveable reaction zone on particulate contact material according to a preferred embodiment of the invention.

A process stream containing the hydrocarbon substrate and the olefinic alkylating agent is passed in line 10 to four-way valve 15 for further distribution of the stream to alkylation reactor 25, controlled by the actual adjustment of the valve. The alkylation reactor 25 is loaded with a fixed bed of particulate polar contact material 26, whereon a reaction zone 27 is established by applying fluorinated sulfonic acid introduced on line 50.

As indicated in the drawing the reaction zone 27 is in an initial cycle of the alkylation process located near end 25a of reactor 26 and the process stream is appropriately introduced via line 11 into reactor 25 at end 25a by adjustment of valve 15 to give passage from line 10 to line 11.

Thereby, the process stream is forced to flow from end 25a through reaction zone 27 to end 25b of reactor 25. In reaction zone 27 the hydrocarbon substrate reacts with the olefinic alkylating agent catalyzed by the fluorinated sulfonic acid adsorbed on the contact material 26. A product stream containing alkylated products is withdrawn in line 20 at end 25b of reactor 25. At the shown adjustment of valve 15 line 20 is connected to product lines 21 and 30 through which the product stream is passed to a storage tank (not shown) or to further processing.

During the initial cycle of the process the reaction zone 27 moves from end 25a to end 25b of reactor 25 by interaction with hydrocarbons in the process stream as described herein before. After having reached a position near end 25b the flow direction of the process stream in reactor 25 is reversed in a subsequent cycle of the alkylation process by adjustment of valve 15 to give passage from line 10 to line 20. At this valve adjustment of the process stream in line 20 is now introduced at end 25b into reactor 25 and the reaction zone 27 is pushed towards end 25a of the reactor. Thereby, the product stream is withdrawn at end 25a of reactor 25 through line 11, which is now connected to line 21 via valve 15.

At the beginning of each process cycle the volume of the process stream, which is introduced into the reactor 25 just before the flow direction, is reversed and has not yet passed through reaction zone 27, will be withdrawn unreacted from reactor 25. This unreacted volume is in the initial phase of each process cycle recycled from line 21 via recycle line 40 to feed line 10.

The above and other advantages of the present invention are further illustrated by the following Examples.

EXAMPLE 1

In this Example isobutane hydrocarbon feed is alkylated with 1-butene alkylating agent by passing a mixed process stream of isobutane and 1-butene in a volume ratio of 9:1 isobutane: 1-butene together with trifluoromethanesulfonic acid ($CF_3SO_3H$) catalyst at a pressure of about 10 bar through a fixed bed reactor, charged with 7 ml silica contact material (Silica Gel 60 with a particle size of 0.063-0.200 mm, supplied by E. Merck, FRG). Before use the contact material has been calcined at 500° C. for one hour.

Six different runs are carried out at different temperatures and flow ratios of the acid catalyst to process stream, calculated on the volume ratio of acid catalyst to 1-butene alkylating agent introduced into the reactor. In each run about 10 ml of the product stream leaving the reactor and containing alkylated products together with minor amounts of spent acid catalyst are washed with about 10 ml of water at ambient. Gas chromatographic analysis of the washed alkylated products reveals composition of the product as set forth in Table 1 below.

A sample of the aqueous washing phase is examined by $^{19}F$-NMR spectroscopic analysis. The NMR-spectra shows only one resonance, which is identical with pure trifluoromethanesulfonic acid obtained in a comparison analysis. The NMR-study indicates that it is possible to recover and regenerate trifluoromethanesulfonic acid from the product stream by washing with water.

In two additional runs the acid catalyst according to the invention is compared to the conventional sulfuric acid ($H_2SO_4$) catalyst in the same experimental set-up as described above. The different process parameters and results obtained in the above experiments are summarized in the following Table:

TABLE 1

| Run | Acid Catalyst | Temp. (C.°) | Flow ratio (vol. acid catalyst/ vol. 1-butene) | Residence Time (min.) | Alkylate yield wt % of 1-butene | Alkylate Composition | | |
|---|---|---|---|---|---|---|---|---|
| | | | | | | $C_5$-$C_7$ (wt %) | $C_8$ (wt %) | $C_9^+$ (wt %) |
| 1 | $CF_3SO_3H$ | 20 | 0.23 | 7 | 191 | 23 | 67 | 10 |
| 2 | $CF_3SO_3H$ | 20 | 0.04 | 4 | 178 | 16 | 72 | 12 |
| 3 | $CF_3SO_3H$ | 20 | 0.06 | 1 | 188 | 25 | 62 | 13 |
| 4 | $CF_3SO_3H$ | 20 | 0.015 | 0.42 | 199 | 17 | 70 | 13 |
| 5 | $CF_3SO_3H$ | 20 | 0.009 | 0.25 | 199 | 23 | 65 | 12 |
| 6 | $CF_3SO_3H$ | 0 | 0.06 | 2 | 164 | 5 | 85 | 10 |
| 8 | $H_2SO_4$ | 20 | 0.41 | 14 | 60 | 9 | 49 | 42 |
| 9 | $H_2SO_4$ | 20 | 0.06 | 2 | 59 | 8 | 58 | 34 |

As apparent from the results listed above even small amounts of trifluoromethanesulfonic acid catalyst provide a substantially quantitative yield of alkylate product, with a high content of desired $C_8$-hydrocarbons resulting in an improved octane value of the obtained alkylated products.

The content of undesired $C_9^+$-fraction in the alkylated products is almost constant under the different process parameters used in the experiments and is appreciable lower than in the alkylated products obtained in the presence of sulfuric acid in comparative runs 8 and 9.

EXAMPLE 2

In this Example a process stream containing ibutane hydrocarbon substrate and 1-butene alkylating agent in a weight ratio of i-butene:1-butene of 9:1 is alkylated in a tubular alkylation reactor in the presence of trifluoromethanesulfonic acid catalyst arranged as moveable reaction zone in the reactor.

In a first experiment the reactor is a Teflon ® tube having an inner diameter of 3.2 mm and a length of 1000 mm. The reactor is filled with 8 ml silica contact material (Silica 60, 70-230 mesh, E. Merck, FRG), which has been calcined at 500° C. for one hour before loading in the reactor tube.

1 ml of the acid catalyst is applied on the contact material at the inlet end of the reactor tube.

Eight different runs are carried out, in each run the process stream is passed in once-through mode at different temperatures through the reactor.

The flow of the process stream is stopped after trifluoromethanesulfonic acid is detected in the effluent from the reactor. After each run about 10 ml of debutanized alkylate product are analyzed by gas chromatography. The operating conditions and the results of each run are summarized in Table 2 below:

In a first experiment a stainless steel reactor tube 25 with an inner diameter of 5.4 mm and a length of 0.5 m is loaded with 8 ml silica contact material (silica 60, 70-230 mesh., E. Merck, FRG) calcined at 500° C. for one hour. 2.0 ml of trifluoromethanesulfonic acid catalyst have been applied at the reactor inlet 25a.

A process stream of i-butane/1-butene (9:1) is passed at a flow rate of 1.85 g/min. through the reactor. After each 23 min. the flow direction of the process stream is reversed as described herein before.

At the beginning of each cycle about 10 ml of the product stream leaving the reactor are recycled back to the reactor inlet.

24 cycles are carried out and the debutanized alkylate product leaving the reactor is analyzed by gas chromatography.

The operating conditions and results of this experiment are summarized in Table 4, which follows.

In a second experiment the reactor of the above ex-

TABLE 2

| Run No. | Acid Cat. Volume (ml) | Temp. (°C.) | Flow rate Process stream g/min. | Residence Time (min.) of Acid Cat. | Number of Cycles | Alkylate yield wt % of 1-butene | Alkylate Composition | | | RON |
|---|---|---|---|---|---|---|---|---|---|---|
| | | | | | | | $C_{5-7}$ (wt %) | $C_8$ (wt %) | $C_{9+}$ (wt %) | |
| 1 | 1 | 52 | 0.48 | 128 | 1 | 149 | 35 | 49 | 16 | n.d.§ |
| 2 | 1 | 42 | 0.52 | 135 | 1 | 157 | 26 | 59 | 15 | n.d. |
| 3 | 1 | 20 | 0.53 | 169 | 1 | 172 | 30 | 53 | 17 | n.d. |
| 4 | 1 | 10 | 0.53 | 223 | 1 | 150 | 13 | 71 | 16 | n.d. |
| 5 | 1 | 0 | 0.55 | 206 | 1 | 165 | 8 | 82 | 10 | n.d. |
| 6 | 1 | −20 | 0.52 | 240 | 1 | 197 | 4 | 88 | 9 | 97 |
| 7 | 1 | −43 | 0.42 | 113 | 1 | 195 | 4 | 83 | 13 | n.d. |
| 8 | 1 | 31 | 0.51 | 172 | 1 | 141 | 13 | 67 | 20 | n.d. |

§ = non determined.

In a second experiment the reactor of the first experiment is replaced by a Teflon ® tube reactor with an inner diameter of 1.6 mm and a length of 4 m, containing 8 ml of the above calcined contact material. Four different runs are carried out. In each run different amounts of the acid catalyst are applied on the contact material at the reactor inlet. As in the first experiment the process stream is passed in once-through mode through the reactor until tribluoromethanesulfonic acid is detected in the reactor effluent. The operating conditions and results of this experiment are summarized in Table 3 below:

periment is replaced by a stainless steel reactor tube with an inner diameter of 5.4 mm and a length of 2 m.

The reactor is loaded with 32 ml of the above calcined silica contact material and 3.0 ml trifluoromethanesulfonic acid catalyst are applied at reactor inlet 25a.

The process stream is passed at a flow rate of 2.5 g/min. through the reactor. In this experiment the flow direction of the process stream is reverted in 15 cycles after each 110 min. 40 ml of the product stream are recycled at the beginning of each cycle.

The operating conditions and results of this experi-

TABLE 3

| Run No. | Acid Cat. Volume (ml) | Temp. (°C.) | Flow rate Process stream g/min. | Residence Time (min.) of Acid Cat. | Number of Cycles | Alkylate yield wt % of 1-butene | Alkylate Composition | | | RON |
|---|---|---|---|---|---|---|---|---|---|---|
| | | | | | | | $C_{5-7}$ (wt %) | $C_8$ (wt %) | $C_{9+}$ (wt %) | |
| 1 | 0.15 | 30 | 0.64 | 74 | 1 | 169 | 21 | 67 | 12 | n.d.§ |
| 2 | 0.08 | 30 | 0.63 | 63 | 1 | 155 | 23 | 63 | 14 | n.d. |
| 3 | 0.14 | 0 | 0.50 | 110 | 1 | 148 | 9 | 82 | 9 | n.d. |
| 4 | 0.11 | −20 | 0.32 | 117 | 1 | 148 | 5 | 87 | 9 | 97 |

§ = non determined.

EXAMPLE 3

In this Example an alkylation process is carried out in accordance with the embodiment of FIG. 2.

ment are summarized in Table 4 below:

TABLE 4

| Experiment No. | Acid Cat. Volume (ml) | Temp. (°C.) | Flow rate Process stream g/min. | Total Residence Time (min.) of Acid Cat. | Number of Cycles | Alkylate yield wt % of 1-butene | Alkylate Composition | | | RON |
|---|---|---|---|---|---|---|---|---|---|---|
| | | | | | | | $C_{5-7}$ (wt %) | $C_8$ (wt %) | $C_{9+}$ (wt %) | |
| 1 | 2.0 | 0 | 1.85 | 555 | 24 | 156 | 13 | 73 | 14 | 96 |
| 2 | 3.0 | 0 | 2.5 | 1663 | 15 | 187 | 14 | 77 | 9 | 96 |

The results obtained by the above experiments summarized in the above Tables clearly show the advantages of the inventive process. Substantially, no loss or disintegration of the fluorated sulfonic acid catalyst is detected, the acid is stable in at least up to 24 cycles, wherein the acid is moved on the contact material between the opposite ends of the reactor.

Thus by periodically reversing the flow direction of the process stream within the alkylation reactor even small amounts of catalyst provide high yields of alkylated products, having a composition comparable to those obtained by once-through alkylation processes as enlisted in Table 1-3 above.

We claim:

1. A process for liquid phase alkylation of a hydrocarbon substrate with an olefinic alkylating agent in the presence of a fluorinated sulfonic acid catalyst in a fixed bed alkylation reactor of particulate polar contact material comprising the steps of:

establishing on the polar contact material a reaction zone with the fluorinated sulfonic acid absorbed on a confined area of the contact material;

passing a process stream of the hydrocarbon substrate and alkylating agent at alkylating conditions in one flow direction through the reactor;

withdrawing a product stream of alkylated products from the reactor; and periodically reversing the flow direction of the process stream as the fluorinated sulfonic acid has passed substantially through the reactor.

2. The process of claim 1, wherein the weight ratio of the acid catalyst and alkylating agent is between 0.001 and 1.

3. The process of claim 1, wherein the particulate polar contact material comprises non-basic refractory material.

4. The process of claim 1, wherein the material is selected from the group consisting of silica, alumina, titania, zirconiz, niobium oxides, tin oxides and mixtures thereof.

5. The process of claim 1, wherein the process stream comprises $C_3$-$C_{10}$ aliphatic hydrocarbons and $C_2$-$C_{10}$ olefins.

6. The process of claim 1, wherein the alkylating conditions include a temperature of between $-50°$ C. and $100°$ C. and a pressure of between 1-100 bar abs. in the alkylation reactor.

7. The process of claim 1, wherein the weight ratio of hydrocarbon substrate and alkylating agent is between 1.5:1 and 30:1.

8. The process of claim 1, further comprising the step of recycling back to the alkylation reactor a part of the product stream, which leaves the alkylation reactor during and immediately after the reversion of the flow direction.

9. The process according to claim 1, wherein the fluorated sulfonic acid catalyst comprises trifluoromethanesulfonic acid and/or fluorosulfonic acid.

10. The process of claim 1 including the steps of separating and recovering spent fluorinated sulfonic acid from the product stream by washing the product stream with water; and recycling the recovered catalyst to the alkylation reaction.

11. The process of claim 2, wherein the weight ratio of the acid catalyst and alkylating agent is between 0.005 and 0.03.

* * * * *